US008420804B2

(12) United States Patent
Balakumar et al.

(10) Patent No.: US 8,420,804 B2
(45) Date of Patent: *Apr. 16, 2013

(54) FORMYL- AND ACETAL-PORPHYRINS BEARING TRIPODAL LINKING GROUPS

(75) Inventors: Arumugham Balakumar, Raleigh, NC (US); Kannan Muthukumaran, Raleigh, NC (US); Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/035,235

(22) Filed: Feb. 25, 2011

(65) Prior Publication Data
US 2011/0152515 A1 Jun. 23, 2011

Related U.S. Application Data

(63) Continuation of application No. 12/362,714, filed on Jan. 30, 2009, now Pat. No. 7,919,615, which is a continuation of application No. 10/867,512, filed on Jun. 14, 2004, now Pat. No. 7,501,507.

(51) Int. Cl.
C07D 487/22 (2006.01)

(52) U.S. Cl.
USPC .......................................................... 540/145

(58) Field of Classification Search .................. 540/145
See application file for complete search history.

(56) References Cited

U.S. PATENT DOCUMENTS

| | | | |
|---|---|---|---|
| 4,230,828 A | 10/1980 | Gaul, Jr. et al. | |
| 5,710,306 A | 1/1998 | Snijder et al. | |
| 5,830,577 A | 11/1998 | Murayama et al. | |
| 5,837,320 A | 11/1998 | Hampden-Smith et al. | |
| 5,959,135 A | 9/1999 | Garner et al. | |
| 6,180,552 B1 | 1/2001 | Hlatky | |
| 6,208,553 B1 | 3/2001 | Gryko et al. | |
| 6,212,093 B1 | 4/2001 | Lindsey | |
| 6,272,038 B1 | 8/2001 | Clausen et al. | |
| 6,324,091 B1 | 11/2001 | Gryko et al. | |
| 6,376,483 B1 * | 4/2002 | Robinson | 514/185 |
| 6,380,421 B1 | 4/2002 | Lu et al. | |
| 6,381,169 B1 | 4/2002 | Bocian et al. | |
| 6,384,229 B1 | 5/2002 | Hlatky | |
| 6,420,648 B1 | 7/2002 | Lindsey | |
| 6,451,942 B1 | 9/2002 | Li et al. | |
| 6,515,161 B1 | 2/2003 | Kreutzer et al. | |
| 6,559,374 B2 | 5/2003 | Lindsey et al. | |
| 6,596,935 B2 | 7/2003 | Lindsey et al. | |
| 6,603,070 B2 | 8/2003 | Lindsey et al. | |
| 6,642,376 B2 | 11/2003 | Lindsey et al. | |
| 6,657,884 B2 | 12/2003 | Bocian et al. | |
| 6,674,121 B2 | 1/2004 | Misra et al. | |
| 6,728,129 B2 | 4/2004 | Lindsey et al. | |
| 6,765,092 B2 | 7/2004 | Lindsey et al. | |
| 6,777,516 B2 | 8/2004 | Li et al. | |
| 6,849,730 B2 | 2/2005 | Lindsey et al. | |
| 6,914,161 B2 | 7/2005 | Beijer et al. | |
| 6,916,982 B2 | 7/2005 | Loewe et al. | |
| 6,924,375 B2 | 8/2005 | Lindsey et al. | |
| 7,501,507 B2 * | 3/2009 | Balakumar et al. | 540/145 |
| 2002/0033192 A1 | 3/2002 | Lindsey et al. | |
| 2002/0137925 A1 | 9/2002 | Lindsey et al. | |
| 2002/0154535 A1 | 10/2002 | Bocian et al. | |
| 2002/0180446 A1 | 12/2002 | Kuhr et al. | |
| 2002/0185173 A1 | 12/2002 | Lindsey et al. | |
| 2003/0075216 A1 | 4/2003 | Loewe et al. | |
| 2003/0081463 A1 | 5/2003 | Bocian et al. | |
| 2003/0092896 A1 | 5/2003 | Lindsey et al. | |
| 2003/0096978 A1 | 5/2003 | Lindsey et al. | |
| 2003/0096989 A1 | 5/2003 | Lindsey et al. | |
| 2003/0104229 A1 | 6/2003 | Li et al. | |
| 2003/0111108 A1 | 6/2003 | Lindsey et al. | |
| 2003/0111670 A1 | 6/2003 | Misra et al. | |
| 2003/0169618 A1 | 9/2003 | Lindsey et al. | |
| 2004/0120180 A1 | 6/2004 | Rotenberg et al. | |
| 2004/0152887 A1 | 8/2004 | Lindsey et al. | |
| 2004/0241584 A1 | 12/2004 | Lindsey | |
| 2004/0244831 A1 | 12/2004 | Lindsey | |
| 2004/0254383 A1 | 12/2004 | Yu et al. | |
| 2005/0019500 A1 | 1/2005 | Bocian et al. | |
| 2005/0038262 A1 | 2/2005 | Lindsey et al. | |
| 2005/0041494 A1 | 2/2005 | Bocian et al. | |
| 2005/0048691 A1 | 3/2005 | Bocian et al. | |
| 2005/0054858 A1 | 3/2005 | Lindsey et al. | |
| 2005/0061641 A1 | 3/2005 | Hernandez et al. | |
| 2005/0062097 A1 | 3/2005 | Misra et al. | |
| 2005/0096465 A1 | 5/2005 | Lindsey et al. | |

OTHER PUBLICATIONS

Greene et al, Protective Groups in Organic Synthesis, $2^{nd}$ edn., John Wiley, N.Y., 1991, pp. 177-182 and 430-432.*

Bhagwat SS et al. Synthesis of thromboxane A2. J. Am. Chem. Soc. 1985: 107: 6372-6376.

Lee C-H et al. Synthetic approaches to regioisomerically pure porphyrins bearing four different meso-substituents. Tetrahedron. 1995; 51(43): 11656-11672.

Trova, Michael P. et al. "Superoxide Dismutase Mimetics. Part 2: Synthesis and Structure-Activity Relationship of Glyoxylate- and Glyoxamide-Derived Metalloporphyrins" *Bioorganic & Medicinal Chemistry* 11 2695-2707 (2003).

Yao Y and Tour J M. Facile convergent route to molecular caltrops. J. Org. Chem. (1999) vol. 64, No. 6, pp. 1968-1971.

Hu J and Mattern D L. Ferrocenyl derivatives with one, two or three sulfur-containing arms for self-assembled monolayer formation. J. Org. Chem. (2000) vol. 65, No. 8, pp. 2278-2281.

(Continued)

*Primary Examiner* — Shaojia Anna Jiang
*Assistant Examiner* — Ganapathy Krishnan
(74) *Attorney, Agent, or Firm* — Myers Bigel Sibley & Sajovec, P.A.

(57) ABSTRACT

A method of making a 5-formylporphyrin, comprises the steps of: condensing a 5-acetaldipyrromethane with a dipyrromethane-1,9-dicarbinol to produce a porphyrin having an acetal group substituted thereon at the 5 position; and then hydrolyzing said porphyrin to produce said 5-formylporphyrin. Products and intermediates useful in such methods, along with methods of making such intermediates, are also described.

6 Claims, No Drawings

OTHER PUBLICATIONS

Gallopini E et al. Long-range electron transfer across molecule-nanocrystalline semiconductor interfaces using tripodal sensitizers. J. Am. Chem. Soc. (2002) vol. 124, No. 26, pp. 7801-7811.

Deng X et al. An efficient convergent synthesis of novel anisotropic adsorbates based on nanometer-sized and tripod-shaped oligophenylene end-capped with triallylsilyl groups. J. Org. Chem. (2002) vol. 67, No. 15, pp. 5279-5283.

Fox M A et al. Fluorescence and redox activity of probes anchored through an aminotrithiol to polycrystalline gold. Langmuir (1998) vol. 14, No. 4, pp. 816-820.

Whitesell J K and Chang H K. Directionally aligned helical peptides on surfaces. Science (Jul. 2, 1993) vol. 261, pp. 73-76.

Siiman O et al. Tris(3-mercaptopropyl)-$N$-glycylaminomethane as a new linker to bridge antibody with metal particles for biological cell separations. Bioconjugate Chem. (2000) vol. 11, No. 4, pp. 549-556.

Hector Jr. L G et al. Investigation of vinyl phosphonic acid/hydroxylated $\alpha$-$Al_2O_3$(0001) reaction enthalpies. Surface Science (2001) vol. 494, pp. 1-20.

Nikitin K et al. Synthesis of tripodal [2]rotaxanes: high concentration principle. Chem. Comm. (2003) pp. 282-284.

Galoppini E et al. Long-distance electron transfer across molecule-nanocrystalline semiconductor interfaces. J. Am. Chem. Soc. (2001) vol. 123, No. 18, pp. 4342-4343.

Greene TW and Wuts PGM. Protective Groups in Organic Synthesis, 2nd edition. John Wiley, 1991, pp. 177-182.

Supplementary European Search Report, EP 05 77 3684, Jun. 16, 2009.

Sazanovich IV et al. Excited-state energy-transfer dynamics of self-assembled imine-linked porphyrin dyads. Inorganic Chemistry. 2003; 42; 6616-6628.

Tkachenko NV et al. Ultrafast photodynamics of exciplex formation and photoinduced electron transfer in porphyrin-fullerene dyads linked at close proximity. Journal of Physical Chemistry A. 2003; 107(42): 8834-8844.

Balaban TS et al. Controlling chirality and optical properties of artificial antenna systems with self-assembling porphyrins. Agnew. Chem. Int. Ed. 2003; 42(19): 2140-2144.

Susumu K et al. Synthesis of novel porphyrin arrays directly-linked through the meso-carbons. Tetrahedron Letters. Nov. 11, 1996; 37(46); 8399-8402.

Osuka A et al. Synthesis of benzochlorin monomer, dimer, and porphyrin-benzochlorin heterodimer from 5-aryl- and 5,15-diaryloctaethylporphyrins. Bull. Chem. Soc. Jpn. 1992; 65(12); 3322-3330.

Smith KM et al. Polyformylation of copper(II) porphyrins. Tetrahedron Letters. 1980; 21: 3747-3750.

Fuhrhop J-H et al. Reactions of oxophlorines and their pi radicals. Journal of the American Chemical Society. Nov. 26, 1975; 97(24): 7141-7152.

Watanabe E et al. Orientation of electrophilic meso-substitution in metallooctaethylporphyrins. Tetrahedron. 1975; 31(11-12): 1385-1390.

Arumugam N et al. Syntheses of regioselectively functionalized, asymmetric porphyrins via a "2+2" condensation. Journal of Porphyrins and Phthalocyanines. Jul. 2002; 6(7): 479-483.

Tamaru S et al. A tin-complexation strategy for use with diverse acylation methods in the preparation of 1,9-diacyldipyrromethanes. Journal of Organic Chemistry. 2004; 69(3): 765-777.

Loewe RS et al. Porphyrins bearing mono or tripodal benzylphosphonic acid tethers for attachment to oxide surfaces. Journal of Organic Chemistry. 2004; 69(5): 1453-1460.

Muthukumaran K et al. Porphyrins bearing arylphosphonic acid tethers for attachment to oxide surfaces. Journal of Organic Chemistry. 2004; 69(5): 1444-1452.

Yu L et al. Excited-state energy-transfer dynamics in self-assembled triads composed of two porphyrins and an intervening bis(dipyrrinato)metal complex. Inorganic Chemistry. 2003; 42(21): 6629-6647.

Gryko D and Lindsey JS. Rational synthesis of meso-substituted porphyrins bearing one nitrogen heterocyclic group. Journal of Organic Chemistry. 2000; 65(7): 2249-2252.

Ema T et al. Selective syntheses of unsymmetrical meso-arylporphyrins. Tetrahedron Letters. 1991; 32(35): 4529-4532.

Maruyama K et al. A synthesis of unsymmetric porphyrin dimers. Bulletin of the Chemical Society of Japan. 1989. 62(10): 3167-3170.

Schwaebe M and Little RD. Asymmetric reductive cyclization. Total synthesis of (−)-C10-desmethyl arteannuin B. J Org Chem. 1996; 61(10): 3240-3244.

Okamoto S et al. An allyltitanium derived from acrolein 1,2-dicyclohexylethylene acetal and ($\eta$2-propene)Ti(O-$i$-Pr2 as a chiral propionaldehyde homoenolate equivalent that reacts with imines with excellent stereoselectivity. An efficient and practical access to optically action $\gamma$-amino carbonyl compounds. J Am Chem Soc. 2001; 123(15): 3462-3471.

Gu T et al. Synthesis and electronic properties of covalent assemblies of oligophenylenevinylene units arising from a calix[4]arene core. J Org Chem. 2001; 66(19): 6432-6439.

Gómez-Escalonilla MJ et al. Synthesis of dumbbell-shaped bis-(pyrazolino[60]fullerene)-oligophenylenevinylene derivatives. Tetrahedron Letters. 2002; 43: 7507-7511.

Kumaresan D et al. Synthesis of 21-thia and 21-oxaporphyrin building blocks and born-dipyrrin appended systems. Tetrahedron. 2002; 58(26): 5347-5356.

* cited by examiner

FORMYL- AND ACETAL-PORPHYRINS BEARING TRIPODAL LINKING GROUPS

RELATED APPLICATIONS

This application claims priority to and is a continuation of U.S. Application Serial No. 12/362,714, filed Jan. 30, 2009, now U.S. Pat. No. 7,919,615, which is a continuation of U.S. patent application Ser. No. 10/867,512, filed Jun. 14, 2004, now U.S. Pat. No. 7,501,507, the disclosure of each of which is incorporated by reference herein in its entirety

GOVERNMENT FUNDING

This invention was made with Government support under grant number GM36238 from the National Institutes of Health. The US Government has certain rights to this invention.

FIELD OF THE INVENTION

The present invention concerns methods and intermediates useful for the manufacture of porphyrin compounds.

BACKGROUND OF THE INVENTION

Formyl-substituted porphyrinic macrocycles provide versatile intermediates and target molecules in bioorganic and materials chemistry. Notable reactions of the porphyrinic formyl group include classical reactions of aldehydes (e.g., Wittig,[1-3] Grignard,[2,4] McMurry,[5] Schiff's base,[6-8] Knoevenage[7,9])[10] as well as reaction with pyrrole or a dipyrromethane leading to multi-porphyrinic architectures.[11] The formyl group also has been exploited in supramolecular chemistry wherein the oxygen of the formyl group binds to the apical site on a neighboring metalloporphyrin.[12] Although a few formyl-porphyrinic compounds occur naturally (e.g., chlorophyll b), most must be synthesized de novo. The generic method for introducing a formyl group to a porphyrinic macrocycle entails Vilsmeier formylation.[10] Vilsmeier formylation, either with the traditional DMF/POCl$_3$[6,13] or the more recent HC(OMe)$_3$/TFA or SnCl$_4$,[3] can only be carried out with metalloporphyrins that are stable toward strong acids (e.g., copper or nickel chelates). Hence formylation typically requires three steps: (1) insertion of copper into a free base porphyrin, (2) formylation of the copper chelate, and (3) demetalation of copper to give the free base porphyrin bearing the formyl group. The removal of copper generally requires strongly acidic conditions such as TFA in H$_2$SO$_4$. The yield of the Vilsmeier formylation is typically quite high (though mixtures of polyformylated metalloporphyrins are known[10,14,15]). However, the requirement for a three-step procedure, use of strong acid, and limited control over the site of formylation presents obvious limitations.

There exists a need for a milder and more direct procedure for preparing formyl porphyrins. Two routes to porphyrins bearing distinct patterns of meso substituents include (1) the self-condensation of a dipyrromethane-1-carbinol affording trans-A$_2$B$_2$-porphyrins,[16] and (2) the reaction of a dipyrromethane and a dipyrromethane-1,9-dicarbinol affording porphyrins with up to four different meso substituents (ABCD-porphyrins).[17]

SUMMARY OF THE INVENTION

A first aspect of the invention is a method of making a 5-formylporphyrin, comprising the steps of: (a) condensing a 5-acetaldipyrromethane with a dipyrromethane-1,9-dicarbinol to produce a porphyrin having an acetal group substituted thereon at the 5 position; and then (b) hydrolyzing the porphyrin to produce the 5-formylporphyrin.

A second aspect of the present invention is a 5-acetaldipyrromethane compound.

A third aspect of the present invention is a 5-acetalporphyrin compound, which in some embodiments has a surface attachment group substituted thereon at the 10 or 15 position.

A fourth aspect of the present invention is a 5-formylporphyrin having a surface attachment group substituted thereon at the 10 or 15 position.

A fifth aspect of the present invention is a method of making a 5,15-diformylporphyrin, comprising the step of: hydrolyzing a 5,15-diacetalporphyrin to produce the 5,15-diformylporphyrin. The 5,15-diacetalporphyrin may be produced by: reducing a 5-acetal-1-acyldipyrromethane to produce a corresponding carbinol; and then self-condensing the carbinol to produce a the 5,15-diacetalprophyrin. The 5-acetal-1-acyldipyrromethane may in turn be produced by acylating a 5-acetal-dipyrromethane with a pyridyl thioester to produce the 5-acetal-1-acyldipyrromethane. In some preferred embodiments the acyl group comprises a surface attachment group.

A sixth aspect of the present invention is a 5-acetal-1-acyldipyrromethane.

A seventh aspect of the present invention is a 5,15-diacetalporphyrin compound, which in some embodiments has a surface attachment group substituted thereon at either or both of the 10 and 20 positions.

An eighth aspect of the present invention is a 5,15-diformylporphyrin having a surface attachment group group substituted thereon at either or both of the 10 and 20 positions.

A ninth aspect of the invention is a method of making a 5,15-diacetalporphyrin, comprising the steps of: acylating a dipyrromethane with a pyridyl thioester of the formula:

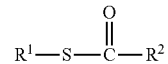

where R$^1$ is 2-pyridyl and R$^2$ is an acetal to produce a 1-(acetalcarbonyl)dipyrromethane; reducing the 1-(acetalcarbonyl)dipyrromethane to produce a 1-(acetalcarbinol)dipyrromethane; and then self-condensing the 1-(acetalcarbinol)dipyrromethane to produce a 5,15-diacetalporphyrin.

A tenth aspect of the invention is a pyridyl thioester of the formula:

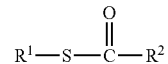

where R$^1$ is 2-pyridyl and R$^2$ is an acetal.

An eleventh aspect of the invention is a 1-(acetalcarbonyl)dipyrromethane, which in some embodiments may be further substituted with a surface attachment group at the 5 position.

A twelfth aspect of the invention is a 1-(acetalcarbinol)dipyrromethane, which in some embodiments may be further substituted with a surface attachment group at the 5 position.

A further aspect of the invention is a method of making a 5,10-diacetalporphyrin, comprising the steps of: acylating a 1-(acetalcarbonyl)dipyrromethane to produce a 1-(acetalcarbonyl)-9-acyldipyrromethane; reducing the a 1-(acetalcarbonyl)-9-acyldipyrromethane to produce a corresponding dicarbinol; condensing the dicarbinol with a dipyrromethane to produce an intermediate; and oxidizing the intermediate to produce a 5,10-diacetalporphyrin. In some embodiments the acyl group comprises a surface attachment group.

A further aspect of the invention is a 1-(acetalcarbonyl) dipyrromethane further substituted with an acyl group at the 9 position, which in some embodiments may be further substituted with a surface attachment group at the 5 position.

A further aspect of the present invention is a 5,10-diacetalporphyrin, which in some embodiments is further substituted with a surface attachment group at either or both of the 15 and 20 positions.

A further aspect of the present invention is a 5,10-diformylporphyrin having a surface attachment group substituted therein at either or both of the 15 and 20 positions.

DETAILED DESCRIPTION OF THE PREFERRED EMBODIMENTS

"Acetal" as used herein refers to a group of the formula:

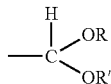

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like, which may be substituted or unsubstituted.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like, which may in turn be substituted or unsubstituted.

"Carbinol" as used herein refers to a group of the formula —CH(—OH)—.

"Carbonyl" as used herein refers to a group of the formula —C(=O)—.

"Dipyrromethane" as used herein includes both unsubstituted and substituted dipyrromethanes, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc. Dipyrromethanes may be coupled to porphyrinic macrocycles at any suitable position on the dipyrromethanes, including the 1, 2, 3, 5, 7, 8, or 9 position.

"Formyl" as used herein refers to a group of the formula —CHO.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including but not limited to compounds of the general formula $LnX_3$ where Ln is a lanthanide and X is halo such as Cl, Br, I, etc., triflate or OTf, etc. Specific examples of Lewis acids that may be used in carrying out the present invention include but are not limited to: $Yb(OTf)_3$, $InCl_3$, $Sc(OTf)_3$, $MgBr_2$ and $CeCl_3$.

"Porphyrin" as used herein refers to a cyclic structure typically composed of four pyrrole rings together with four nitrogen atoms and two replaceable hydrogens for which various metal atoms can readily be substituted. A typical porphyrin is hemin.

"Surface attachment group" as used herein refers to a functional group having a protected or unprotected reactive site or group on the group such as a carboxylic acid, alcohol, thiol, selenol or tellurol group, or a phosphono (e.g. dihydroxyphosphoryl), alkenyl (e.g., ethenyl) and alkynyl (e.g., ethynyl) group. Examples of surface attachment groups (with the reactive site or group in unprotected form) include but are not limited to:

4-carboxyphenyl,
carboxymethyl,
2-carboxyethyl,
3-carboxypropyl,
2-(4-carboxyphenyl)ethynyl,
4-(2-(4-carboxyphenyl)ethynyl)phenyl,
4-carboxymethylphenyl,
4-(3-carboxypropyl)phenyl,
4-(2-(4-carboxymethylphenyl)ethynyl)phenyl;
4-hydroxyphenyl,
hydroxymethyl,
2-hydroxyethyl,
3-hydroxypropyl,
2-(4-hydroxyphenyl)ethynyl,
4-(2-(4-hydroxyphenyl)ethynyl)phenyl,
4-hydroxymethylphenyl,
4-(2-hydroxyethyl)phenyl,
4-(3-hydroxypropyl)phenyl,
4-(2-(4-hydroxymethylphenyl)ethynyl)phenyl;
4-mercaptophenyl,
mercaptomethyl,
2-mercaptoethyl,
3-mercaptopropyl,
2-(4-mercaptophenyl)ethynyl,
4-(2-(4-mercaptophenyl)ethynyl)phenyl,
4-mercaptomethylphenyl,
4-(2-mercaptoethyl)phenyl,
4-(3-mercaptopropyl)phenyl,
4-(2-(4-mercaptomethylphenyl)ethynyl)phenyl;
4-selenylphenyl,
selenylmethyl,
2-selenylethyl,
3-selenylpropyl,
2-(4-selenylphenyl)ethynyl,
4-selenylmethylphenyl,
4-(2-selenylethyl)phenyl,
4-(3-selenylpropyl)phenyl,
4-selenylmethylphenyl,
4-(2-(4-selenylphenyl)ethynyl)phenyl;
4-tellurylphenyl,
tellurylmethyl,
2-tellurylethyl,
3-tellurylpropyl,
2-(4-tellurylphenyl)ethynyl,
4-(2-(4-tellurylphenyl)ethynyl)phenyl,
4-tellurylmethylphenyl,
4-(2-tellurylethyl)phenyl, 4-(3-tellurylpropyl)phenyl,
4-(2-(4-tellurylmethylphenyl)ethynyl)phenyl;
4-(dihydroxyphosphoryl)phenyl,
(dihydroxyphosphoryl)methyl,
2-(dihydroxyphosphoryl)ethyl,
3-(dihydroxyphosphoryl)propyl,
2-[4-(dihydroxyphosphoryl)phenyl]ethynyl,
4-[2-[4-(dihydroxyphosphoryl)phenyl]ethynyl]phenyl,
4-[dihydroxyphosphoryl)methyl]phenyl,
4-[2-(dihydroxyphosphoryl)ethyl]phenyl,
4-[2-[4-(dihydroxyphosphoryl)methylphenyl]ethynyl]phenyl;
4-(hydroxy(mercapto)phosphoryl)phenyl,
(hydroxy(mercapto)phosphoryl)methyl,
2-(hydroxy(mercapto)phosphoryl)ethyl,
3-(hydroxy(mercapto)phosphoryl)propyl,
2-[4-(hydroxy(mercapto)phosphoryl)phenyl]ethynyl,
4-[2-[4-(hydroxy(mercapto)phosphoryl)phenyl]ethynyl]phenyl,
4-[(hydroxy(mercapto)phosphoryl)methyl]phenyl,
4-[2-(hydroxy(mercapto)phosphoryl)ethyl]phenyl,
4-[2-[4-(hydroxy(mercapto)phosphoryl)methylphenyl]ethynyl]phenyl;
4-cyanophenyl,
cyanomethyl,
2-cyanoethyl,
3-cyanopropyl,
2-(4-cyanophenyl)ethynyl,
4-[2-(4-cyanophenyl)ethynyl]phenyl,
4-(cyanomethyl)phenyl,
4-(2-cyanoethyl)phenyl,
4-[2-[4-(cyanomethyl)phenyl]ethynyl]phenyl;
4-cyanobiphenyl;
4-aminophenyl,
aminomethyl,
2-aminoethyl,
3-aminopropyl,
2-(4-aminophenyl)ethynyl,
4-[2-(4-aminophenyl)ethynyl]phenyl,
4-aminobiphenyl;
4-formylphenyl,
4-bromophenyl,
4-iodophenyl,
4-vinylphenyl,
4-ethynylphenyl,
4-allylphenyl,
4-[2-(trimethylsilyl)ethynyl]phenyl,
4-[2-(triisopropylsilyl)ethynyl]phenyl,
4-(4,4,5,5-tetramethyl-1,3,2-dioxaborolan-2-yl)phenyl;
formyl,
bromo,
iodo,
bromomethyl,
chloromethyl,
ethynyl,
vinyl,
allyl;
4-(ethynyl)biphen-4'-yl,
4-[2-(triisopropylsilyl)ethynyl]biphen-4'-yl,
3,5-diethynylphenyl;
4-(bromomethyl)phenyl,
2-bromoethyl;

In addition to the monodentate linker-surface attachment groups described above, multidentate linkers can be employed [Nikitin, K. *Chem. Commun.* 2003, 282-283; Hu, J.; Mattern, D. L. *J Org. Chem.* 2000, 65, 2277-2281; Yao, Y.; Tour, J. M. *J. Org. Chem.* 1999, 64, 1968-1971; Fox, M. A. et al. *Langmuir,* 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science,* 2001, 494, 1-20; Whitesell, J. K.; Chang, H. K. *Science,* 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device in an upright configuration on a planar surface. Specific examples of such linkers are built around the triphenylmethane or tetraphenylmethane unit, including the following:

1,1,1-tri[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl]methyl}phenyl,
1,1,1-tris[4-(dihydroxyphosphorylmethyl)phenyl]methyl,
4-{1,1,1-tris[4-(dihydroxyphosphorylmethyl)phenyl]methyl}phenyl.

Applicants specifically intend the disclosures of all US Patent references cited herein to be incorporated by reference herein in their entirety.

(A) Synthesis of 5-Formylporphyrins and intermediates for making the same. Condensation steps as described herein below may be carried out in accordance with known techniques. The reaction conditions of the present invention are not critical. In general, the reactions may be carried out at any suitable temperature and pressure, such as room temperature and ambient pressure. In general the reactions are rapid (e.g., are carried out for a time of from 1 to 10 minutes), and preferably are carried out within a time of 1 to 2 hours, as some scrambling may ultimately occur if the reactions are carried out for an unduly long period of time (e.g., more than one to two days, depending upon the particular conditions). In some embodiments solvents which may be used to carry out the present invention preferably have a dielectric constant of about 20, 15, or 10 or less, at room temperature (i.e., 25° C.). The solvent may be a single compound or mixtures thereof. Preferably the solvent is non-aqueous. Particular examples of suitable solvents include, but are not limited to, chlorinated aliphatic hydrocarbons (e.g., dichloromethane, chloroform, 1,2-dichloroethane, 1,1,1-trichloroethane, 1,1,2,2-tetrachloroethane, 1,1-dichloroethylene, cis-1,2-dichloroethylene, trans-1,2-dichloroethylene, trichloroethylene, etc.); chlorinated aromatic hydrocarbons (e.g., chlorobenzene, 1,2-dichlorobenzene, 1,3-dichlorobenzene, 1,4-dichlorobenzene, 1-chloronaphthalene, etc.); hydrocarbons (e.g., benzene, toluene, xylene, ethylbenzene, mesitylene, durene, naphthalene); ethers (e.g., ethyl ether, propyl ether, tetrahydrofuran, p-dioxane, anisole, phenyl ether, etc.); esters (e.g., ethyl acetate, methyl acetate, ethyl benzoate, butyl phthalate, etc.); glymes (e.g., 2-methoxyethanol, 2-butoxyethanol), and other solvents such as carbon disulfide, tributyl borate, etc., and mixtures of the foregoing. Note that some solvents may be less preferred: for example, an oxygen in diethyl ether may coordinate with and tie up the Lewis acid, and hence be less preferred. Some embodiments utilize a Lewis acid catalyst. Any suitable electron-pair acceptor may be used as the Lewis acid catalyst in the present invention, including, but not limited to, $CsCl$, $SmCl_3 \cdot 6H_2O$, $InCl_3$, $CrF_3$, $AlF_3$, $Sc(OTf)_3$, $TiF_4$, $BEt_3$, $GeI_4$, $EuCl_3 \cdot nH_2O$, $LaCl_3$, $Ln(OTf)_3$ where Ln=a lanthanide, etc. The concentration may range, for example, from 0.001 or 0.01 mmol/L to 100 or 500 mmol/L, or more. Specific examples of Lewis acids and suitable concentrations thereof include $InCl_3$ (0.32 mmol/L), $Sc(OTf)_3$ (0.32 mmol/

L), Yb(OTf)$_3$ (1.0 mmol/L), and Dy(OTf)$_3$ (0.32 mmol/L). See, e.g., Lindsey et al., US Patent Application 2003/0096978 (May 22, 2003).

As noted above, the present invention provides a method of making a 5-formylporphyrin (one example of which is shown in Scheme 1 below), comprising the steps of: condensing a 5-acetaldipyrromethane with a dipyrromethane-1,9-dicarbinol to produce a porphyrin having an acetal group substituted thereon at the 5 position; hydrolyzing the porphyrin to produce the 5-formylporphyrin. The condensing step is carried out in a polar or nonpolar solvent in the presence of a Lewis acid followed by oxidation with an oxidizing agent such as DDQ in accordance with known techniques. The hydrolyzing step may be carried out in any suitable manner, such as with a biphasic mixture of CH$_2$Cl$_2$, TFA and water at room temperature.

The dipyrromethane-1,9-dicarbinol may be produced by reducing a 1,9-diacyldipyrromethane to foam the dipyrromethane-1,9-dicarbinol, and the 5-acetaldipyrromethane may be produced by reacting glyoxal with neopentyl glycol to provide a mixture of monoacetal and bis-acetal; and then reacting the mixture with excess pyrrole to produce the 5-acetaldipyrromethane, both in accordance with known techniques. As noted above, in some preferred embodiments the dipyrromethane-1,9-dicarbinol has a surface attachment group substituted thereon at the 5 position.

Intermediates described herein thus include 5-acetaldipyrromethane compounds and 5-acetalporphyrin compounds, including 5-acetalporphyrins having a surface attachment group substituted thereon at the 10 or 15 position.

Products produced by these methods include 5-formylporphyrins having a surface attachment group substituted thereon at the 10 or 15 position.

(B) Synthesis of 5,15-Diformylporphyrins and intermediates for making the same. The present invention further provides a method of making a 5,15-diformylporphyrin, one example of which is exemplified by Scheme 2 below. In general, the method comprises the step of: hydrolyzing a 5,15-diacetalporphyrin to produce the 5,15-diformylporphyrin.

The 5,15-diacetalporphyrin may be produced by reducing a 5-acetal-1-acyldipyrromethane to produce a corresponding carbinol; and then self-condensing the carbinol to produce a the 5,15-diacetalprophyrin.

The 5-acetal-1-acyldipyrromethane may in turn be produced by acylating a 5-acetal-dipyrromethane with a pyridyl thioester to produce the 5-acetal-1-acyldipyrromethane (again in some preferred embodiments the acyl group comprises a surface attachment group).

Intermediates used in such processes include 5-acetal-1-acyldipyrromethanes and 5,15-diacetalporphyrin compounds, particularly including those having a surface attachment group substituted thereon at either or both of the 10 and 20 positions. Such intermediates and methods provide 5,15-diformylporphyrins having a surface attachment group group substituted thereon at either or both of the 10 and 20 positions.

Another aspect of the invention is a method of making a 5,15-diacetalporphyrin, which in one embodiment is exemplified by Schemes 3-4 below. Such methods generally comprise the steps of: acylating a dipyrromethane with a pyridyl thioester of the formula:

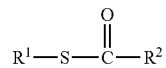

where R$^1$ is 2-pyridyl and R$^2$ is an acetal to produce a 1-(acetalcarbonyl)dipyrromethane; reducing the 1-(acetalcarbonyl)dipyrromethane to produce a 1-(acetalcarbinol)dipyrromethane; and then self-condensing the 1-(acetalcarbinol) dipyrromethane to produce a 5,15-diacetalporphyrin. The methods preferably further comprise the step of: hydrolyzing the 5,15-diacetalporphyrin to produce a 5,15-diformylprophyrin.

The pyridyl thioester may be is produced by reacting an acetal-acid with 2,2'-dipyridyldisulfide and Ph$_3$P to produce the pyridyl thioester in accordance with known techniques.

Such methods provide as useful intermediates 1-(acetalcarbonyl)dipyrromethanes (such as exemplified by compound 13 below), which may be further substituted with a surface attachment group at the 5 position, along with the corresponding 1-(acetalcarbinol)dipynomethanes, (such as exemplified by compound 13-OH below), which again may be further substituted with a surface attachment group at the 5 position.

These methods provide 5,15-diacetalporphyrins as intermediates, including those further substituted with a surface attachment group at either or both the 10 and 20 position.

(C) Synthesis of 5,10-diformylporphyrins and intermediates useful therein. A method of making a 5,10-diacetalporphyrin (one example of which is exemplified by Scheme 5 below), comprises the steps of: acylating a 1-(acetalcarbonyl) dipyrromethane to produce a 1-(acetalcarbonyl)-9-acyldipyrromethane; reducing the 1-(acetalcarbonyl)-9-acyldipyrromethane to produce a corresponding dicarbinol; condensing the dicarbinol with a dipyrromethane to produce an intermediate; oxidizing the intermediate to produce a 5,10-diacetalporphyrin. In some embodiments the the acyl group preferably comprises a surface attachment group. Again the method may further comprise the step of hydrolyzing the 5,10-diacetalporphyrin to produce a 5,10-diformylporphyrin.

Such methods provide as useful intermediates 1-(acetalcarbonyl)dipyrromethanes further substituted with an acyl group at the 9 position (on example of which is compound 16 below), which in preferred embodiments may be further substituted with a surface attachment group at the 5 position.

Such methods further provide as useful intermediates 5,10-diacetalporphyrins, including in preferred embodiments those further substituted with a surface attachment group at either or both of the 15 and 20 positions.

Such methods provide as products 5,10-diformylporphyrins having a surface attachment group substituted therein at either or both of the 15 and 20 positions.

(D) Utility. Porphyrin ring compounds or porphyrinic macrocycles are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Porphyrinic macrocycles are also useful immobilized to a substrate for making charge storage molecules and information storage devices containing the same. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The porphyrinic macrocycle may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting Examples.

EXAMPLES

Results and Discussion

5-Formylporphyrins. We initially examined the use of a 5-(dithiolan-2-yl)dipyrromethane as a precursor to porphyrins bearing a latent formyl group, but upon porphyrin formation the meso-dithiolane group was partially lost yielding a mixture of porphyrins (see Supporting Information). While the origin of the fragmentation reaction was not clear, we turned to the use of an acetal protecting group. The acid-catalyzed reaction of glyoxal with neopentyl glycol provided a mixture of the monoacetal 1[19] and the bis-acetal. Our efforts to isolate the monoacetal from the crude reaction mixture by distillation provided the glyoxal monoacetal 1 in only 4% yield rather than the reported yield of 50%.[19] Treatment of 1 with excess pyrrole in the presence of InCl$_3$ following a standard procedure[20] afforded the acetal-dipyrromethane 2 in 70% yield. Given the difficulty of isolating pure 1 and the ease of isolation of 2, crude 1 was employed directly in the dipyrromethane-forming reaction. In this manner, 2 was obtained from glyoxal in 32% overall yield.

The condensation of dipyrromethane 2 with 3-diol (prepared by the NaBH$_4$ reduction of 1,9-diacyldipyrromethane 3; Ar=p-tert-butylphenyl) was carried out in the standard manner[17,21] in the presence of InCl$_3$ followed by oxidation with DDQ. Acetal-porphyrin 4 was obtained cleanly in 13% yield. Hydrolysis of the acetal in porphyrin 4 was carried out using a biphasic mixture of CH$_2$Cl$_2$, TFA, and water (10:1:1)[22] at room temperature to afford meso-formyl porphyrin 5 in 92% yield. Metalation of 5 with Zn(OAc)$_2$·2H$_2$O gave the zinc porphyrin Zn-5 in 92% yield (Schemes 1a-1b).

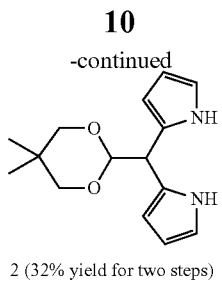

2 (32% yield for two steps)

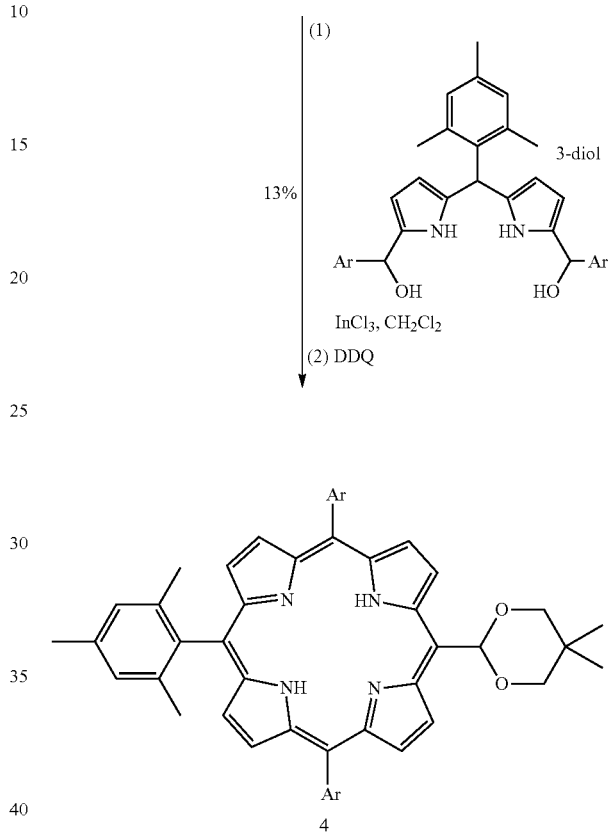

Scheme 1a

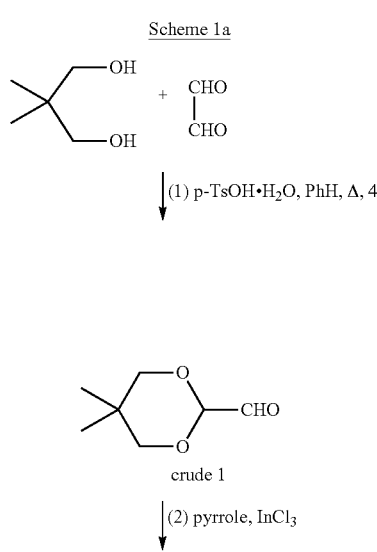

Scheme 1b

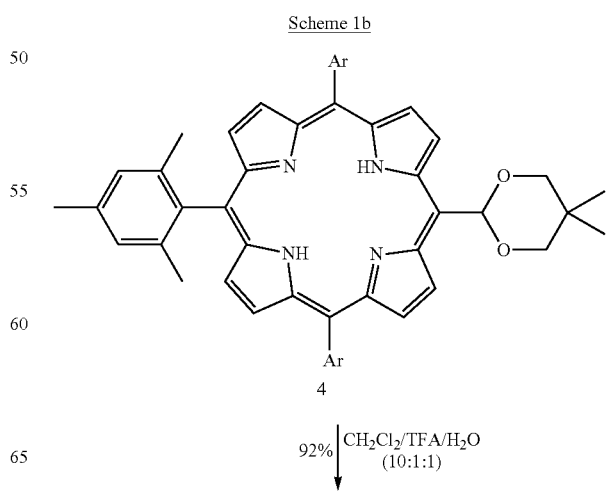

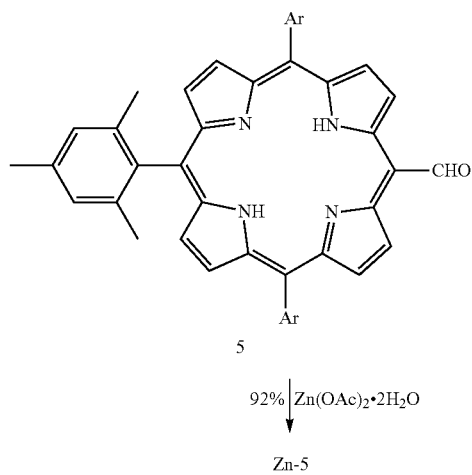

5

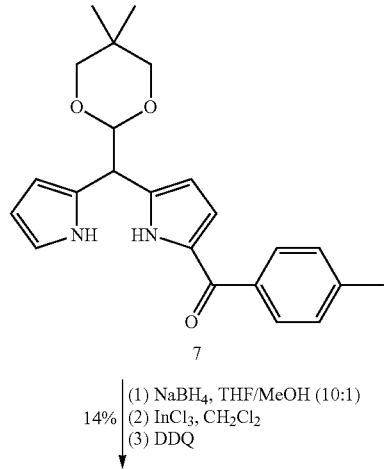

7

92% | Zn(OAc)₂·2H₂O (1) NaBH₄, THF/MeOH (10:1)
14% | (2) InCl₃, CH₂Cl₂
(3) DDQ

Zn-5

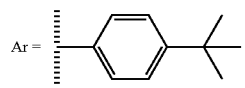

Ar =

5,15-Diformylporphyrins. Two routes were investigated for the synthesis of 5,15-diformylporphyrins. Each route employs the self-condensation of the carbinol derived from a 1-acyldipyrromethane. The routes differ only in whether the acetal group is located at the 5-position or attached to the 1-acyl group of the 1-acyldipyrromethane.

The route that employs a dipyrromethane-monocarbinol bearing the acetal at the 5-position begins with dipyrromethane 2. Treatment of 2 under the standard conditions for 1-acylation[16] with pyridyl thioester 6 afforded the 1-acyldipyrromethane 7 in 72% yield. Reduction of 7 with NaBH₄ and self-condensation[16,21] of the resulting dipyrromethane-monocarbinol 7-OH in the presence of InCl₃ followed by oxidation with DDQ gave porphyrin 8 in 14% yield. Hydrolysis of the two acetal groups in porphyrin 8 with CH₂Cl₂/TFA/H₂O (10:1:1) gave 5,15-diformylporphyrin 9 in 90% yield (Scheme 2).

8: R =

90% | CH₂Cl₂/TFA/H₂O
     (10:1:1)

9: R = CHO

Scheme 2

2

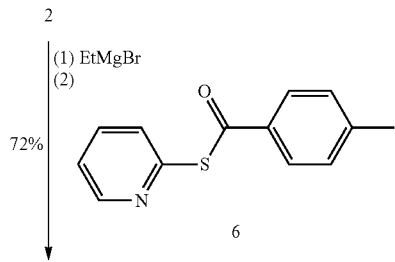

(1) EtMgBr
(2)

72%

6

The route that employs a dipyrromethane-monocarbinol bearing the acetal at the 1-carbinol position requires the synthesis of an appropriate acetal-containing Mukaiyama reagent. The reaction of glyoxylic acid monohydrate with neopentyl glycol in the presence of Amberlyst-15 ion-exchange resin (as described for homologous compounds)[23] provided a mixture of the desired acetal-acid 10 and an acetal-ester byproduct. Hydrolysis of the mixture with 20% aqueous NaOH afforded 10 in 73% yield. The Mukaiyama reaction[24] of 10 with 2,2'-dipyridyldisulfide and Ph₃P provided pyridyl thioester 11, which proved difficult to purify. The crude reaction mixture containing 11 was used in the next step. Thus, acylation of 5-phenyldipyrromethane (12) in the standard manner[16] with the crude 11 afforded the 1-acyldipyrromethane 13 in 64% yield (Scheme 3).

Scheme 3

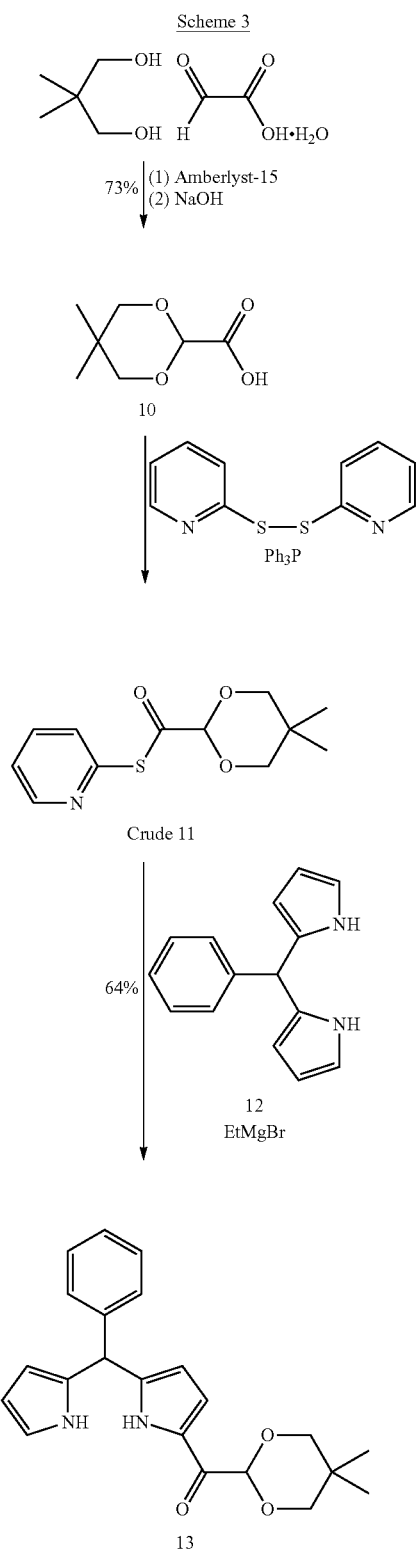

Reduction of 13 with NaBH$_4$ gave the dipyrromethane-monocarbinol 13-OH, which upon self-condensation[16,21] in the presence of InCl$_3$ followed by oxidation with DDQ provided porphyrin 14 in 21% yield. Hydrolysis of the two acetal groups in porphyrin 14 in CH$_2$Cl$_2$/TFA/H$_2$O (5:1:1) afforded the 5,15-diformylporphyrin 15 in 83% yield (Scheme 4).

Scheme 4

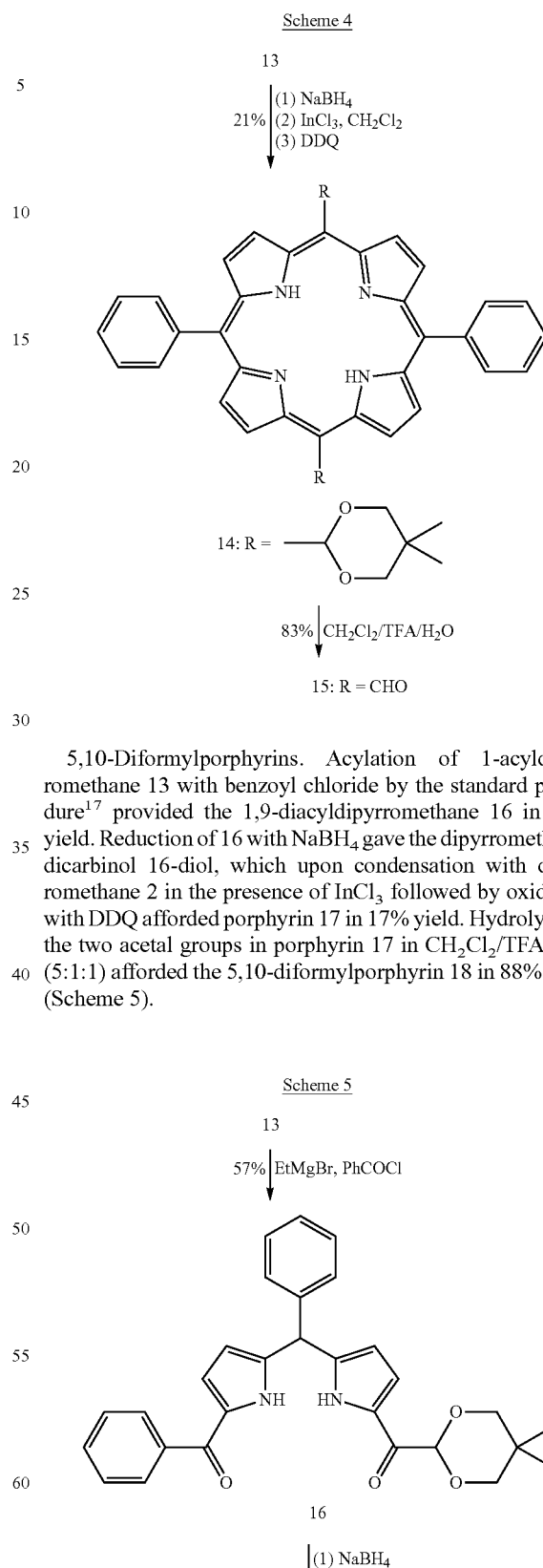

5,10-Diformylporphyrins. Acylation of 1-acyldipyrromethane 13 with benzoyl chloride by the standard procedure[17] provided the 1,9-diacyldipyrromethane 16 in 57% yield. Reduction of 16 with NaBH$_4$ gave the dipyrromethane-dicarbinol 16-diol, which upon condensation with dipyrromethane 2 in the presence of InCl$_3$ followed by oxidation with DDQ afforded porphyrin 17 in 17% yield. Hydrolysis of the two acetal groups in porphyrin 17 in CH$_2$Cl$_2$/TFA/H$_2$O (5:1:1) afforded the 5,10-diformylporphyrin 18 in 88% yield (Scheme 5).

Scheme 5

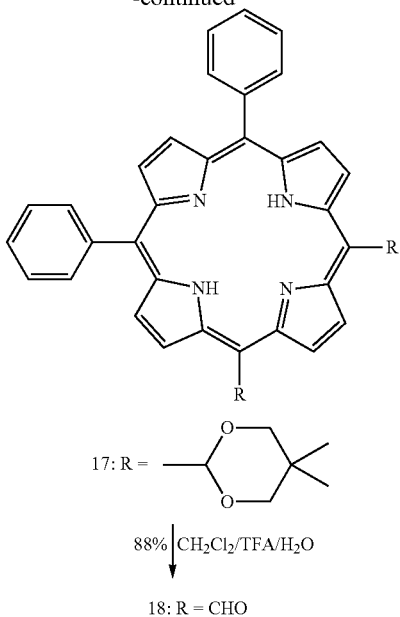

17: R = [5,5-dimethyl-1,3-dioxan-2-yl group]

88% | CH₂Cl₂/TFA/H₂O

18: R = CHO

Spectroscopic characterization. Each porphyrin was characterized by absorption spectroscopy, $^1$H NMR spectroscopy, $^{13}$C NMR spectroscopy (except 9 and 15 owing to poor solubility), laser-desorption mass spectrometry (LD-MS),[25] and FAB-MS. The acetal-substituted porphyrins (4, 8, 14, 17) exhibited typical absorption spectra, with the characteristic Soret band in the 416-419 nm region. The corresponding formyl-porphyrins exhibited red-shifted Soret bands. The magnitude of the shift varied from 9 nm (one formyl, 5), to ~12 nm (5,15-diformyl, 9, 15), to 23 nm (5,10-diformyl, 18). The IR spectra showed bands at 1672 cm$^{-1}$ to 1674 cm$^{-1}$ (one formyl, 5; 5,15-diformyl, 15; 5,10-diformyl, 18) and at 1666 cm$^{-1}$ (5,15-diformyl, 9). In each formyl-porphyrin, the formyl proton resonated as a distinctive singlet at 12.3-12.5 ppm. The formyl carbon gave a resonance at 195.13 ppm (one formyl, 5) and at 194.77 ppm (5,10-diformyl, 18). Each porphyrin gave the expected molecule ion peak upon LD-MS analysis.

Conclusions. Acetal-substituted dipyrromethane, dipyrromethane-1-carbinol, and dipyrromethane-1,9-dicarbinol components can be used in rational routes for forming porphyrins. Gentle acid hydrolysis of the resulting meso-acetal porphyrins affords the corresponding meso-formyl porphyrins. The conversion of acetal-substituted dipyrromethane species to free base porphyrins complements the traditional Vilsmeier formylation of metalloporphyrins.

Experimental Section.

Noncommercial compounds. Compounds 3,[17] 6,[16] and 12[20] were prepared as described in the literature.

2-Formyl-5,5-dimethyl-1,3-dioxane (1). A mixture of glyoxal (10.0 g of 40 wt. % aqueous solution, 0.070 mol), 2,2-dimethyl-1,3-propanediol (7.28 g, 0.070 mol) and p-toluenesulfonic acid (0.260 g, 1.36 mmol) in benzene (140 mL) was refluxed for 4 h in a flask fitted with a Soxhlet extractor containing Na$_2$SO$_4$. Then the reaction mixture was treated with solid NaHCO$_3$ (0.250 g, 2.90 mmol) and filtered. The filtrate was concentrated and vacuum distilled (Kugelrohr) to afford a colorless liquid (413 mg, 4%). The $^1$H NMR spectrum was consistent with the data reported in a patent.[19] This reactive compound was used immediately in the next reaction.

5-(5,5-Dimethyl-1,3-dioxan-2-yl)dipyrromethane (2). Following a standard procedure,[20] a sample of 1 (0.40 g, 2.7 mmol) was condensed in pyrrole (19 mL, 0.27 mol) containing InCl$_3$ (61 mg, 0.27 mmol) under argon at room temperature for 1.5 h. The reaction mixture was worked up by addition of NaOH (0.33 g, 8.3 mmol), filtration, recovery of excess pyrrole from the filtrate, trituration of the resulting residue with hexanes to remove traces of pyrrole, and crystallization [ethanol/water (4:1)], affording a pale yellow solid (504 mg, 70%): mp 112-114° C.; $^1$H NMR δ 0.74 (s, 3H), 1.15 (s, 3H), 3.51 (d, J=11 Hz, 2H), 3.572 (d, J=11 Hz, 2H), 4.42 (d, J=2 Hz, 1H), 4.85 (d, J=2 Hz, 1H), 5.92 (m, 2H), 6.13 (m, 2H), 6.73 (m, 2H), 8.75 (s, 2H); $^{13}$C NMR δ 129.3, 117.3, 107.9, 107.6, 103.8, 77.6, 42.0, 30.5, 23.4, 21.9; Anal. Calcd for C$_{15}$H$_{20}$N$_2$O$_2$: C, 69.20; H, 7.74; N, 10.76. Found: C, 69.23; H, 7.71; N, 10.73.

Streamlined Synthesis of 5-(5,5-Dimethyl-1,3-dioxan-2-yl)dipyrromethane (2). A mixture of glyoxal (10.0 g of 40 wt. % aqueous solution, 0.070 mol), 2,2-dimethyl 1,3-propanediol (7.28 g, 0.070 mol) and p-toluenesulfonic acid (0.260 g, 1.36 mmol) in benzene (140 mL) was refluxed for 4 h in a flask fitted with a Soxhlet extractor containing Na$_2$SO$_4$. Then the reaction mixture was treated with solid NaHCO$_3$ (0.250 g, 2.90 mmol) and filtered. The filtrate was concentrated, affording crude 2-formyl-5,5-dimethyl-1,3-dioxane (1). The crude 1 was treated with pyrrole (223 mL, 3.45 mol; an amount corresponding to an assumed yield of 50% for the glyoxal monoacetal) and the standard reaction for dipyrromethane formation[20] was carried out. InCl$_3$ (0.762 g, 3.45 mmol) was added and the mixture was stirred under argon at room temperature for 1.5 h. The reaction mixture was worked up by addition of NaOH (4.13 g, 103 mmol), filtration, recovery of excess pyrrole from the filtrate, trituration of the resulting residue with hexanes to remove traces of pyrrole, and chromatography [silica, hexanes/CH$_2$Cl$_2$/ethyl acetate (7:2: 1)], affording a pale yellow solid (2.84 g, 32%): mp 112-114° C.; $^1$H NMR δ 0.74 (s, 3H), 1.15 (s, 3H), 3.51 (d, J=11 Hz, 2H), 3.57 (d, J=11 Hz, 2H), 4.42 (d, J=2 Hz, 1H), 4.85 (d, J=2 Hz, 1H), 5.92 (m, 2H), 6.13 (m, 2H), 6.73 (m, 2H), 8.75 (s, 2H); Anal. Calcd for C$_{15}$H$_{20}$N$_2$O$_2$: C, 69.20; H, 7.74; N, 10.76. Found: C, 69.18; H, 7.77; N, 10.71.

5,15-Bis(4-tert-butylphenyl)-10-(5,5-dimethyl-1,3-dioxan-2-yl)-20-mesitylporphyrin (4). Following a general procedure,[17,21] reduction of diacyldipyrromethane 3 (0.584 g, 1.00 mmol) in THF/methanol (44 mL, 10:1) with NaBH$_4$ (0.756 g, 20.0 mmol) gave the corresponding dicarbinol 3-diol. Condensation of 3-diol and 2 (0.260 g, 1.00 mmol) was performed in CH$_2$Cl$_2$ (400 mL) containing InCl$_3$ (88.4 mg, 0.400 mmol) for 1 h followed by oxidation with DDQ (340 mg, 1.50 mmol) for 1 h. Methanol (40 mL) and TEA (4 mL) were added. The reaction mixture was filtered (alumina pad, CH$_2$Cl$_2$). The filtrate was concentrated and chromatographed (silica, CH$_2$Cl$_2$/hexanes), affording a purple solid (104.6 mg, 13%): $^1$H NMR δ –2.78 (s, 2H), 1.12 (s, 3H), 1.62 (s, 18H), 1.83 (s, 6H), 1.92 (s, 3H), 2.62 (s, 3H), 4.33 (m, 4H), 7.26 (s, 4H), 7.75 (d, J=8.0 Hz, 4H), 7.95 (s, 1H), 8.12 (d, J=8.0 Hz, 4H), 8.79 (d, J=4.0 Hz, 2H), 8.98 (d, J=4.0 Hz, 2H), 9.91 (s, 2H); $^{13}$C NMR δ 151.2, 150.7, 139.6, 139.5, 139.2, 138.7, 138.3, 137.9, 134.6, 134.4, 128.0, 127.9, 124.0, 123.8, 120.2, 119.7, 111.7, 106.6, 80.4, 35.2, 35.1, 31.9, 31.9, 31.2, 25.2, 22.8, 21.9, 21.8, 21.7; LD-MS obsd 809.18; FAB-MS obsd 806.4580, calcd 806.4560 (C$_{55}$H$_{58}$N$_4$O$_2$); λ$_{abs}$ 419, 514, 547, 591, 648 nm.

5,15-Bis(4-tert-butylphenyl)-10-formyl-20-mesitylporphyrin (5). Following a general procedure,[22] a solution of 4 (43 mg, 0.05 mmol) in CH$_2$Cl$_2$ (5 mL) was treated with TFA/water (0.5 mL, 1:1) to give a biphasic solution. After stirring at room temperature for 2.5 h, $CH_2Cl_2$ was added. The organic layer was washed (saturated aqueous $NaHCO_3$ and brine), dried ($Na_2SO_4$), concentrated, and chromatographed (silica, $CH_2Cl_2$/hexanes) to give a purple solid (34.8 mg, 92%): IR (neat) 1674, 1557, 1110 cm$^{-1}$; $^1$H NMR δ−1.90 (s, 2H), 1.61 (s, 18H), 1.84 (s, 6H), 2.61 (s, 3H), 7.26 (s, 2H), 7.75-7.78 (m, 4H), 8.08-8.11 (m, 4H), 8.59 (d, J=4.4 Hz, 2H), 8.69 (d, J=4.4 Hz, 2H), 9.01 (d, J=5.2 Hz, 2H), 10.03 (br s, 2H), 12.50 (s, 1H); $^{13}$C NMR δ195.1, 151.2, 139.2, 138.7, 138.3, 137.7, 134.2, 128.0, 124.4, 124.0, 122.6, 107.7, 35.2, 31.9, 29.9, 21.8, 21.7; LD-MS obsd 721.86; FAB-MS obsd 721.3931, calcd 720.3828 ($C_{50}H_{48}N_4O$); $\lambda_{abs}$ 428, 528, 567, 600, 657 nm.

Zn(II)-5,15-Bis(4-tert-butylphenyl)-10-formyl-20-mesitylporphyrin (Zn-5). A solution of porphyrin 5 (0.080 g, 0.11 mmol) in $CHCl_3$/MeOH (10:1) was treated with Zn(OAc)$_2$·2H$_2$O (0.12 g, 0.55 mmol). Standard workup including chromatography (silica, $CH_2Cl_2$) afforded a greenish-purple solid (80 mg, 92%): IR (neat) 2918, 1615, 1549 cm$^{-1}$; $^1$H NMR δ1.62 (s, 18H), 1.82 (s, 6H), 2.61 (s, 3H), 7.25 (s, 4H), 7.76 (d, J=8.0 Hz, 4H), 8.69 (d, J=8.0 Hz, 4H), 8.78 (d, J=4.8 Hz, 2H), 9.05 (d, J=4.8 Hz, 2H), 9.94 (d, J=4.8 Hz, 2H), 12.30 (s, 1H); $^{13}$C NMR δ195.7, 153.3, 152.1, 150.8, 149.3, 149.2, 139.3, 139.1, 138.6, 137.9, 135.1, 134.3, 132.4, 131.8, 129.1, 127.9, 123.8, 35.1, 31.9, 21.8, 21.7; LD-MS obsd 780.81; FAB-MS obsd 782.2985, calcd 782.2963 ($C_{50}H_{46}N_4OZn$); $\lambda_{abs}$ 431, 561, 602 nm.

5-(5,5-Dimethyl-1,3-dioxan-2-yl)-1-(p-toluoyl)dipyrromethane (7). Following a general procedure,[16] a solution of 2 (1.30 g, 5.00 mmol) in THF (5 mL) under argon was treated dropwise with EtMgBr (12.5 mL, 12.5 mmol, 1.0 M solution in THF) at room temperature, then cooled to −78° C. A solution of 6 (1.15 g, 5.00 mmol) in THF (5 mL) was added over 1 min. The solution was maintained at −78° C. for 10 min and then allowed to warm to room temperature. The standard workup including chromatography (silica, $CH_2Cl_2$/ethyl acetate) afforded a pale yellow amorphous solid (1.362 g, 72%): mp 60-62° C.; $^1$H NMR δ0.72 (s, 3H), 1.16 (s, 3H), 2.41 (s, 3H), 3.46-3.48 (m, 2H), 3.69-3.77 (m, 2H), 4.47 (d, J=2.8 Hz, 1H), 4.89 (d, J=3.2 Hz, 1H), 5.97-5.98 (m, 1H), 6.03-6.04 (m, 1H), 6.12-6.15 (m, 1H), 6.72-6.77 (m, 2H), 7.26 (d, J=8.0 Hz, 2H), 7.79 (d, J=8.0 Hz, 2H), 8.94 (s, 1H), 10.16 (s, 1H); $^{13}$C NMR δ184.3, 142.3, 137.7, 136.1, 130.9, 129.2, 129.1, 127.6, 119.3, 118.0, 110.9, 108.1, 103.1, 77.7, 77.6, 42.3, 30.5, 23.3, 22.0, 21.8; Anal. Calcd for $C_{23}H_{26}N_2O_3$: C, 72.99; H, 6.92; N, 7.40. Found: C, 72.55; H, 6.92; N, 7.45.

5,15-Bis(5,5-dimethyl-1,3-dioxan-2-yl)-10,20-bis(p-tolyl)porphyrin (8). Following a general procedure,[16,21] reduction of 7 (0.567 g, 1.50 mmol) in THF/methanol (30 mL, 3:1) with NaBH$_4$ (1.41 g, 37.3 mmol) gave the corresponding dipyrromethane-monocarbinol 7-OH as a dark yellow oil. The self-condensation of 7-OH was performed in $CH_2Cl_2$ (283 mL) containing InCl$_3$ (20.0 mg, 90.4 μmol) at room temperature for 5 min followed by oxidation with DDQ (510 mg, 2.25 mmol) for 1 h. Methanol (10 mL) and TEA (1 mL) were added. The reaction mixture was filtered (alumina pad, $CH_2Cl_2$). The filtrate was concentrated and chromatographed (silica, $CH_2Cl_2$/hexanes) to give a purple solid (149.8 mg, 14%): $^1$H NMR δ−2.97 (s, 2H), 1.11 (s, 6H), 1.90 (s, 6H), 2.72 (s, 6H), 4.30-4.31 (m, 8H), 7.55 (d, J=8.0 Hz, 4H), 7.90 (s, 2H), 8.05 (d, J=8.0 Hz, 4H), 8.93 (d, J=4.8 Hz, 4H), 9.89 (d, J=5.2 Hz, 4H); $^{13}$C NMR δ139.9, 137.5, 134.7, 132.3, 129.0, 127.5, 120.4, 113.0, 106.2, 80.3, 31.2, 25.1, 22.8, 21.8; LD-MS obsd 719.82; FAB-MS obsd 718.3549, calcd 718.3519 ($C_{46}H_{46}N_4O_4$); $\lambda_{abs}$ 416, 512, 544, 590, 643 nm.

5,15-Diformyl-10,20-bis(p-toluoyl)porphyrin (9). As described for 5, a solution of 8 (72 mg, 1.0 mmol) in $CH_2Cl_2$ (10 mL) was treated with TFA/water (1.0 mL, 1:1) at room temperature for 3 days. The standard workup including chromatography (silica, $CH_2Cl_2$/hexanes) afforded a purple green solid (48.6 mg, 90%): IR (neat) 1666, 1551, 1122 cm$^{-1}$; $^1$H NMR δ−2.31 (s, 2H), 2.74 (s, 6H), 7.61 (d, J=8.0 Hz, 4H), 8.05 (d, J=8.0 Hz, 4H), 9.00 (d, J=5.2 Hz, 4H), 10.00 (d, J=5.2 Hz, 4H), 12.53 (s, 2H); LD-MS obsd 547.09; FAB-MS obsd 547.2131, calcd 547.2134 ($C_{36}H_{26}N_4O_2$); $\lambda_{abs}$ 429, 584, 684 nm.

2-Carboxy-5,5-dimethyl-1,3-dioxane (10). Following a general procedure,[23] a mixture of glyoxylic acid monohydrate (5.0 g, 54 mmol), 2,2-dimethyl 1,3-propanediol (8.5 g, 81 mmol) and Amberlyst-15 ion-exchange resin (100 mg) in benzene (140 mL) was refluxed for 15 h in a flask fitted with a Dean-Stark apparatus. The reaction mixture was filtered. The filtrate was concentrated and then refluxed with 20% aqueous NaOH (50 mL) for 30 min. The resulting alkaline solution was extracted with ether and neutralized in the cold with dilute HCl. At the end the pH was brought to ∼1.0 using H$_3$PO$_4$. The acidified aqueous layer was extracted with ether. The extracts were combined, dried ($Na_2SO_4$) and concentrated to afford a white solid (6.349 g, 73%): mp 58-60° C.; $^1$H NMR δ0.80 (s, 3H), 1.22 (s, 3H), 3.57 (d, J=12.0 Hz, 2H), 3.79 (d, J=12.0 Hz, 2H), 4.97 (s, 1H); $^{13}$C NMR δ169.1, 124.7, 95.8, 77.5, 30.6, 23.0, 21.9; FAB-MS obsd 161.0806, calcd 161.0814 ($C_7H_{12}O_4$).

1-[(5,5-Dimethyl-1,3-dioxan-2-yl)carbonyl]-5-phenyl-dipyrromethane (13). Following general procedures,[16,24] a solution of 10 (0.50 g, 3.1 mmol), 2,2′-dipyridyldisulfide (1.0 g, 4.6 mmol) and triphenylphosphine (1.2 g, 4.6 mmol) in THF (10 mL) was stirred at room temperature for 24 h under argon. The resulting mixture was added dropwise to a solution of 12 (2.1 g, 9.4 mmol) and EtMgBr (24 mL, 24 mmol, 1.0 M solution in THF) in THF (10 mL) at −78° C. followed by reaction at room temperature for 1 h. Standard workup including chromatography [silica, $CH_2Cl_2$/ethyl acetate (7:3)] afforded a pale yellow solid (732 mg, 64%): mp 154-156° C.; $^1$H NMR δ0.78 (s, 3H), 1.21 (s, 3H), 3.56 (d, J=12.0 Hz, 2H), 3.75 (d, J=12.0 Hz, 2H), 5.10 (s, 1H), 5.52 (s, 1H), 5.95 (d, J=0.8 Hz, 1H), 6.07 (d, J=2.4 Hz, 1H), 6.14 (d, J=2.0 Hz, 1H), 6.67-6.68 (m, 1H), 7.15-7.31 (m, 6H), 8.39 (s, 1H), 9.78 (s, 1H); $^{13}$C NMR δ181.2, 140.7, 130.9, 128.9, 128.6, 127.5, 120.7, 118.0, 111.0, 108.6, 107.8, 100.5, 77.7, 77.7, 44.2, 30.8, 23.3, 22.0; Anal. Calcd for $C_{22}H_{24}N_2O_3$: C, 72.50, H, 6.64, N, 7.69. Found: C, 72.52, H, 6.69, N, 7.63.

5,15-Bis(5,5-dimethyl-1,3-dioxan-2-yl)-10,20-diphenylporphyrin (14). As described for 8, a sample of 13 (300 mg, 0.824 mmol) was reduced with NaBH$_4$ (780 mg, 21.0 mmol) in THF/methanol (16 mL, 3:1) for 15 min. The resulting 13-OH (a pale yellow oil) was subjected to self-condensation in $CH_2Cl_2$ (164 mL) containing InCl$_3$ (11.0 mg, 49.7 μmol) at room temperature for 30 min followed by oxidation with DDQ (280 mg, 1.23 mmol) for 1 h. Standard workup including chromatography [silica, $CH_2Cl_2$/ethyl acetate (98:2)] gave a purple solid (60.3 mg, 21%): $^1$H NMR δ−2.96 (s, 2H), 1.10 (s, 6H), 1.90 (s, 6H), 4.30-4.31 (m, 8H), 7.75-7.78 (m, 6H), 7.91 (s, 2H), 8.16-8.18 (m, 4H), 8.90 (d, J=4.0 Hz, 4H), 9.90 (d, J=4.0 Hz, 4H); $^{13}$C NMR δ142.8, 134.7, 132.3, 129.2, 127.9, 126.7, 120.3, 113.1, 106.2, 80.4, 31.2, 25.1, 22.8; LD-MS obsd 691.93; FAB-MS obsd 691.3318, calcd 691.3284 ($C_{44}H_{42}N_4O_4$); $\lambda_{abs}$ 416, 512, 541, 589, 641 nm.

5,15-Diformyl-10,20-diphenylporphyrin (15). As described for 5, a solution of 14 (30 mg, 44 μmol) in $CH_2Cl_2$ (5.0 mL) was treated with TFA/water (2.0 mL, 1:1) with stirring at room temperature for 3 days. Standard workup including chromatography (silica, $CH_2Cl_2$/ethyl acetate) gave a purple green solid (18.7 mg, 83%): IR (neat) 1673, 1550, 1120 cm$^{-1}$; $^1$H NMR δ−2.30 (s, 2H), 7.80-7.82 (m, 6H), 8.17-8.19 (m, 4H), 8.59 (d, J=4.8 Hz, 4H), 10.02 (s, 4H), 12.55 (s, 2H); LD-MS obsd 518.90, calcd 518.1743 ($C_{34}H_{22}N_4O_2$); $\lambda_{abs}$ 428, 538, 584, 622, 684 nm.

1-Benzoyl-9-[(5,5-dimethyl-1,3-dioxan-2-yl)carbonyl]-5-phenyldipyrromethane (16). Following a general procedure,[17] a solution of 13 (500 mg, 1.37 mmol) in THF (10 mL) was treated dropwise with EtMgBr (2.75 mL, 2.75 mmol, 1.0 M solution in THF) at room temperature under argon for 10 min. Benzoyl chloride (160 μL, 2.75 mmol) was added. After 10 min, additional EtMgBr (1.37 mL, 1.37 mmol, 1.0 M solution in THF) and benzoyl chloride (80.0 μL, 1.37 mmol) were added. After 30 min, the standard workup including chromatography [silica, $CH_2Cl_2$/ethyl acetate (7:3)] afforded a dark yellow solid (364.7 mg, 57%): mp 112-114° C.; $^1$H NMR δ0.80 (s, 3H), 1.23 (s, 3H), 3.60 (d, J=11.2 Hz, 2H), 3.79 (d, J=11.2 Hz, 2H), 5.15 (s, 1H), 5.57 (s, 1H), 6.06-6.11 (m, 2H), 6.78-6.80 (m, 1H), 7.17-7.55 (m, 9H), 7.82-7.84 (m, 2H), 9.57 (s, 2H); $^{13}$C NMR δ184.7, 139.5, 139.3, 138.4, 132.0, 131.2, 129.4, 129.1, 128.6, 128.5, 128.1, 120.4, 111.3, 111.0, 100.6, 77.7, 44.6, 30.8, 23.3, 22.1; Anal. Calcd for $C_{29}H_{28}N_2O_4$: C, 74.34, H, 6.02, N, 5.98. Found: C, 73.45, H, 6.14, N, 5.73.

5,10-Bis(5,5-dimethyl-1,3-dioxan-2-yl)-15,20-diphenylporphyrin (17). As described for 4, reduction of 16 (200 mg, 0.420 mmol) in THF/methanol (32 mL, 3:1) with NaBH$_4$ (800 mg, 21.0 mmol) for 15 min gave 16-diol as a dark yellow oil. Condensation of 16-diol and 2 (111 mg, 0.420 mmol) was carried out in $CH_2Cl_2$ (170 mL) containing InCl$_3$ (37.5 mg, 177 μmol) for 15 min followed by oxidation with DDQ (143 mg, 0.634 mmol) for 1 h. The standard workup afforded a purple solid (49.8 mg, 17%): $^1$11 NMR δ−2.93 (s, 2H), 1.13 (s, 6H), 1.95 (s, 6H), 4.30-4.37 (m, 8H), 7.71-7.77 (m, 6H), 7.95 (s, 2H), 8.15-8.18 (m, 4H), 8.73 (s, 2H), 8.94 (d, J=4.4 Hz, 2H), 9.96 (s, 2H), 10.01 (s, 2H); $^{13}$C NMR δ142.3, 134.7, 128.0, 126.9, 121.6, 112.0, 106.6, 80.5, 31.2, 25.3, 22.9; LD-MS obsd 691.86; FAB-MS obsd 691.3291, calcd 691.3284 ($C_{44}H_{42}N_4O_4$); $\lambda_{abs}$ 417, 511, 586 nm.

5,10-Diformyl-15,20-diphenylporphyrin (18). As described for 5, a solution of 17 (30 mg, 44 μmol) in $CH_2Cl_2$ (5.0 mL) was treated with TFA/water (2.0 mL, 1:1) at room temperature for 3 days. The standard workup including chromatography (silica, CHCl$_3$/hexanes) afforded a purple solid (19.8 mg, 88%): IR (neat) 1672, 1548, 1166 cm$^{-1}$; $^1$H NMR δ−2.19 (s, 2H), 7.76-7.83 (m, 6H), 8.15-8.17 (m, 4H), 8.66 (s, 2H), 8.93 (d, J=4.8 Hz, 2H), 9.79 (s, 2H), 9.89 (s, 2H), 12.28 (s, 2H); $^{13}$C NMR δ194.8, 141.0, 134.5, 128.7, 127.2, 109.7, 100.1; LD-MS obsd 519.18; FAB-MS obsd 519.1839, calcd 519.1821 ($C_{34}H_{22}N_4O_2$); $\lambda_{abs}$ 440, 535, 607, 655 nm.

5-(dithiolan-2-yl)dipyrromethane was synthesized in accordance with standard techniques.

REFERENCES (1) (a) Callot, H. J. *Tetrahedron* 1973, 29, 899-901. (b) Arnold, D. P.; Gaete-Holmes, R.; Johnson, A. W.; Smith, A. R. P.; Williams, G. A. *J. Chem. Soc. Perkin. Trans.* 1 1978, 1660-1670. (c) Burrell, A. K.; Officer, D. L. *Synlett* 1998, 1297-1307.

(2) Arnold, D. P.; Johnson, A. W.; Mahendran, M. *J. Chem. Soc., Perkin. Trans.* 1 1978, 366-370.

(3) (a) Montforts, F.-P.; Scheurich, G.; Meier, A.; Haake, G.; Höper, F. *Tetrahedron Lett.* 1991, 32, 3477-3480. (b) Ando, A.; Yamazaki, M.; Komura, M.; Sano, Y.; Hattori, N.; Omote, M.; Kumadaki, I. *Heterocycles* 1999, 50, 913-918.

(4) Runge, S.; Senge, M. O. *Tetrahedron* 1999, 55, 10375-10390.

(5) (a) Vicente, M. G. H.; Smith, K. M. *J. Org. Chem.* 1991, 56, 4407-4418. (b) Jaquinod, L.; Nurco, D. J.; Medforth, C. J.; Pandey, R. K.; Forsyth, T. P.; Olmstead, M. M.; Smith, K. M. *Angew. Chem. Int. Ed. Engl.* 1996, 35, 1013-1016.

(6) Johnson, A. W.; Oldfield, D. *J. Chem. Soc. (C)* 1966, 794-798.

(7) Witte, L.; Fuhrhop, J.-H. *Angew. Chem. Int. Ed.* 1975, 14, 361-363.

(8) (a) Ponomarev, G. V. *Chem. Heterocyclic Compounds* 1996, 32, 1263-1280. (b) Ponomarev, G. V.; Morozova, Y. V.; Yashunsky, D. V. *Chem. Heterocyclic Compounds* 2001, 37, 253-255.

(9) Schlözer, R.; Fuhrhop, J.-H. *Angew. Chem. Int. Ed.* 1975, 14, 363.

(10) Ponomarev, G. V. *Chem. Heterocyclic Compounds* 1994, 30, 1444-1465.

(11) (a) Wasielewski, M. R.; Johnson, D. G.; Niemczyk, M. P.; Gaines, G. L., III; O'Neil, M. P.; Svec, W. A. *J. Am. Chem. Soc.* 1990, 112, 6482-6488. (b) Johnson, D. G.; Niemczyk, M. P.; Minsek, D. W.; Wiederrecht, G. P.; Svec, W. A.; Gaines, G. L., III; Wasielewski, M. R. *J. Am. Chem. Soc.* 1993, 115, 5692-5701.

(12) Balaban, T. S.; Bhise, A. D.; Fischer, M.; Linke-Schaetzel, M.; Roussel, C.; Vanthuyne, N. *Angew. Chem. Int. Ed.* 2003, 42, 2140-2144.

(13) Inhoffen, H. H.; Fuhrhop, J.-H.; Voigt, H.; Brockmann H., Jr. *Justus Liebigs Annalen Chem.* 1966, 695, 133-143.

(14) (a) Ponomarev. G. V.; Kirillova, G. V.; Maravin, G. B.; Babushkina, T. A.; Suboch, V. P. *Chem. Heterocyclic Compounds* 1979, 15, 622-629. (b) Ponomarev. G. V.; Kirillova, G. V.; Maravin, G. B.; Babushkina, T. A.; Suboch, V. P. *Ibid.* 630-633.

(15) (a) Smith, K. M., Bisset, G. M. F., Tabba, H. D. *J. Chem. Soc., Perkin. Trans.* 1 1982, 581-585. (b) Smith, K. M.; Bisset, G. M. F.; Case, J. J.; Tabba, H. D. *Tetrahedron Lett.* 1980, 21, 3747-3750.

(16) Rao, P. D.; Littler, B. J.; Geier, G. R., III; Lindsey, J. S. *J. Org. Chem.* 2000, 65, 1084-1092.

(17) Rao, P. D.; Dhanalekshmi, S.; Littler, B. J.; Lindsey, J. S. *J. Org. Chem.* 2000, 65, 7323-7344.

(18) Trova, M. P.; Gauuan, P. J. F.; Pechulis, A. D.; Bubb, S. M.; Bocckino, S. B.; Crapo, J. D.; Day, B. J. *Bioorg. Med. Chem.* 2003, 11, 2695-2707.

(19) Blanc, A.; Hamedi-Sangsari, F.; Chastrette, F. J. U.S. Pat. No. 4,835,320.

(20) Laha, J. K.; Dhanalekshmi, S.; Taniguchi, M.; Ambroise, A.; Lindsey, J. S. *Org. Process Res. Dev.* 2003, 7, 799-812.

(21) Geier, G. R., III; Callinan, J. B.; Rao, P. D.; Lindsey, J. S. *J. Porphyrins Phthalocyanines* 2001, 5, 810-823.

(22) Lindsey, J. S.; Brown, P. A.; Siesel, D. A. *Tetrahedron* 1989, 45, 4845-4866.

(23) Newman, M. S.; Chen, C. H. *J. Org. Chem.* 1973, 38, 1173-1177.

(24) Nicolaou, K. C.; Claremon, D. A.; Papahatjis, D. P. *Tetrahedron Lett.* 1981, 22, 4647-4650.

(25) (a) Fenyo, D.; Chait, B. T.; Johnson, T. E.; Lindsey, J. S. *J. Porphyrins Phthalocyanines* 1997, 1, 93-99. (b) Srinivasan, N.; Haney, C. A.; Lindsey, J. S.; Zhang, W.; Chait, B. T. *J. Porphyrins Phthalocyanines* 1999, 3, 283-291.

The foregoing is illustrative of the present invention, and is not to be construed as limiting thereof. The invention is defined by the following claims, with equivalents of the claims to be included therein.

That which is claimed is:

1. A 5-acetalporphyrin having a surface attachment group substituted thereon at the 10 or 15 position, wherein said surface attachment group is a tripodal linker bearing thiol, carboxylic acid, alcohol, or phosphonic acid units.

2. A 5-formylporphyrin having a surface attachment group substituted thereon at the 10 or 15 position, wherein said surface attachment group is a tripodal linker bearing thiol, carboxylic acid, alcohol, or phosphonic acid units.

3. A 5,15-diacetalporphyrin having a surface attachment group substituted thereon at either or both of the 10 and 20 positions, wherein said surface attachment group is a tripodal linker bearing thiol, carboxylic acid, alcohol, or phosphonic acid units.

4. A 5,15-diformylporphyrin having a surface attachment group substituted thereon at either or both of the 10 and 20 positions, wherein said surface attachment group is a tripodal linker bearing thiol, carboxylic acid, alcohol, or phosphonic acid units.

5. A 5,10-diacetalporphyrin further substituted with a surface attachment group at either or both of the 15 and 20 positions, wherein said surface attachment group is a tripodal linker bearing thiol, carboxylic acid, alcohol, or phosphonic acid units.

6. A 5,10-diformylporphyrin having a surface attachment group substituted therein at either or both of the 15 and 20 positions, wherein said surface attachment group is a tripodal linker bearing thiol, carboxylic acid, alcohol, or phosphonic acid units.

* * * * *